United States Patent [19]
Röchling et al.

[11] 3,988,465
[45] Oct. 26, 1976

[54] BENZIMIDAZOLE INSECTICIDES

[75] Inventors: Hans F. W. Röchling; Karl-Heinz Büchel; Friedrich W.A.G.K. Korte, all of Hangelar, Germany

[73] Assignee: Shell Oil Company, Houston, Tex.

[22] Filed: Nov. 14, 1974

[21] Appl. No.: 523,956

Related U.S. Application Data

[62] Division of Ser. No. 542,204, April 13, 1966, Pat. No. 3,884,933.

[52] U.S. Cl. .............................. 424/273; 260/309.2
[51] Int. Cl.² .......................................... A01N 9/22

[58] Field of Search.................. 260/309.2; 424/273

[56] References Cited
FOREIGN PATENTS OR APPLICATIONS
659,384   5/1965   Belgium ......................... 260/309.2

*Primary Examiner*—V. D. Turner

[57] ABSTRACT

Substituted benzimidazole-1-carboxylic acid esters, such as 2-trifluoromethyl-4,5,6-trichloro-1-benzimidazole carboxylic acid methyl ester, are useful as herbicides and insecticides.

5 Claims, No Drawings

BENZIMIDAZOLE INSECTICIDES

This is a division of application Ser. No. 542,204, filed Apr. 13, 1966, now issued as U.S. Pat. No. 3,884,933.

The novel esters of this invention are characterized by the generic formula:

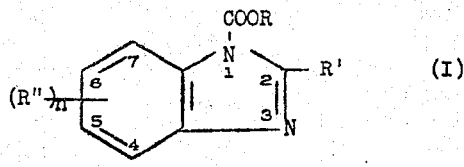

wherein R contains up to 12 carbon atoms and is alkyl, alkenyl, cycloalkyl, aryl, aralkyl, or alkaryl, or one of these substituted by one or more of halogen, particularly chlorine or bromine, nitro, or alkoxy R'' is a negative substituent such as halogen or polyhaloalkyl, R' is halogen, particularly chlorine or bromine, nitro, cyano or amino ($-NH_2$, $-NHR$, $-NRR$), $n$ is 1, 2, 3 or 4, in which if $n$ is greater than 1, each of R'' is the same or is different.

Where R represents alkyl or alkenyl, it may suitably be either straight-chain or branched-chain in configuration. Likewise, any alkyl or alkylene moiety involved in the group R can be of either straight-chain or branched-chain configuration. When R is aralkyl, the alkylene moiety preferably contains not more than four carbon atoms between the carbon of the aryl moiety and the oxygen atom of the carboxy moiety. When R involves an aromatic moiety, preferably that moiety is the phenyl group. Typical examples of suitable hydrocarbon groups represented by R thus include: methyl, ethyl, n- and isopropyl, allyl, methallyl, crotyl, n-, sect, tert-, and isobutyl, the various isomeric butenyl and pentenyl groups, the isomeric $C_5$-, $C_6$-, $C_7$-, $C_8$-, $C_9$- and $C_{10}$-alkyl and alkenyl groups, cycloalkyl groups such as the cyclopentyl, isomeric methyl- and ethylcyclopentyl groups, the cyclohexyl groups, isomeric methyl-, ethyl- and dimethyl-cyclohexyl groups, the cycloheptyl group and the like, phenyl, naphthyl, the isomers of methylphenyl, the isomeric dimethylphenyls, the ethylphenyls, benzyl, the methylbenzyls, phenethyl, alpha-methylbenzyl, and the like. Typical examples of suitable substituted groups represented by R include: 2-chloroethyl, 2-bromoethyl, 3-chloropropyl, 2-chloropropyl, 2,3-dichloropropyl, 2-methoxyethyl, bromomethyl, chloromethyl, 3-nitropropyl, the isomers of chlorophenyl, dibromophenyl, methoxyphenyl, methoxyhexyl, and the like. High biological activity appears to be associated with low molecular weight; consequently, it is preferred that the group, R, contain no more than 8 carbon atoms, and, further, that it be hydrocarbon in character. The highest biological activity appears to be associated with those compounds of the invention wherein R represents alkyl of from 1 to 4 carbon atoms.

When R' represents polyhaloalkyl, it preferably contains from 1 to 4 carbon atoms. Preferably, it represents perhaloalkyl, and still more preferably, perfluoroalkyl, although the halogen may be chlorine, bromine, and/or iodine, as well. Because of their very high biological activity, compounds of the invention wherein R' is trifluoromethyl are preferred.

While R'' may be any halogen, preferably it is bromine or chlorine. When R'' is amino other than $-NH_2$, it preferably is mono- or di-alkylamino in which each alkyl contains from 1 to 4 carbon atoms.

Because of high biological activity, a preferred subgenera of the esters of the invention consists of those members wherein R is alkyl, alkenyl, cycloalkyl, aryl, aralkyl or alkaryl hydrocarbon of up to 8 carbon atoms, R' is trifluoromethyl, R'' is chlorine or bromine and $n$ is 2 to 4. Because of their very high biological activity, a preferred subclass of this subgenera comprises those esters wherein R is alkyl of from 1 to 4 carbon atoms, R'' is chlorine and $n$ is 3.

Typical species of the esters, of the invention, illustrating and exemplifying the genus, are set forth in the working examples.

The esters of the invention are prepared according to the process of the invention by reacting a benzimidazole (an acid) of the formula:

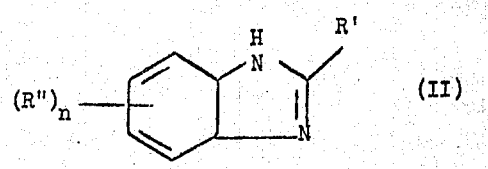

wherein the symbols have the respective meanings already given, with an alkali metal ethylate in an inert solvent into the alkali metal salt thereof and by converting this salt with a haloformic acid ester, RO-(O)CCl. The conversion of the acid benzimidazole with the alkali metal ethylate into the alkali metal salt and the reaction of the latter with the haloformic acid esters may, without previous isolation, be carried out in such a way that the corresponding benzimidazole is dissolved in an inert solvent and reacted with stirring at room temperature with the equivalent amount of alkali metal ethylate. Subsequently the corresponding haloformic acid ester is likewise added in molar proportion at a moderately elevated temperature, preferably between 25° and 50° C. After filtration of the resulting alkali metal chloride and evaporation of the solvent the resulting ester may be isolated.

The esters of the invention are generally solid substances, which are soluble in acetone, alcohols, ligroin and other solvents, and which may be purified from these by recrystallization.

The substituted benzimidazoles used as starting material for the process according to the invention may be prepared in a manner similar to that of a slightly modified process described by W. T. Smith and I. C. Steinle in J. Am. Chem. Soc., Volume 75 (1953), page 1292, from o-phenyl diamines by conversion with the correspondingly substituted carboxylic acids, the substituent of the carboxylic acid component entering the imidazole ring as a group R'. On the one hand the substituent or the substituents R'' may be present, either partly or completely, in the o-phenylene diamine reaction component or, on the other hand, be introduced into the benzene ring by suitable measures after the ring has been closed to form the bicyclic heterocyclic compound. The 2-trifluoromethyl-4,5,6-trichloro benzimidazole required as starting material for the preparation of a 2-trifluoromethyl-4,5,6-trichloro-1-benzimidazole carboxylic acid ester may be prepared for example either by reaction of 3,4,5-trichloro-o-phenylene diamine with trifluoroacetic acid or form o-phenylene diamine with trifluoroacetic acid and subsequent chlorination. The following provides an example of the latter mode of carrying out the reaction.

A quantity of 432 grams (4 moles) of o-phenylene diamine and 570 grams (5 moles) of trifluoroacetic acid was dissolved in concentrated hydrochloric acid (32% HCl) and refluxed for 15 hours. After being cooled the resultant 2-trifluoromethyl benzimidazole precipitated in crystalline form. The crystals were removed by suction, washed with water and subsequently dried. Yield: 714 grams. By concentration and neutralization of the filtrate with ammonia a further 30 grams were obtained. Total yield: 100%, melting point: 208° C. Analysis (% by weight):

|  | C | H | N | F |
|---|---|---|---|---|
| Calculated: | 51.63 | 2.7 | 15.05 | 30.62 |
| Found: | 51.50 | 3.0 | 15.3 | 29.7 |

To chlorinate the 2-trifluoromethyl benzimidazole, 186 grams (1 mole) of the crude product of the previous step was dissolved in water with heating, subsequently refluxed, elemental chlorine being added slowly to the boiling solution over a period of 18 hours. After the solution had been cooled the chlorinated product precipitated in the form of colourless to pale yellow crystals. The thin layer chromatogram and the gas chromatographic analysis showed that the product consisted of 95% of theory of 4,5,6-trichloro-2-trifluoromethyl benzimidazole. Minor amounts of similarly formed 4,5,6,7-tetrachloro-2-trifluoromethyl benzimidazole were easily separated by means of recrystallization from xylene. The 4,5,6-trichloro-2-trifluoromethyl benzimidazole was purified by dissolving it in hot methanol and precipitating it with water. Yield: 275 grams (95% of theory), melting point: 240°–242° C. Analysis (% by weight):

|  | C | H | N | Cl |
|---|---|---|---|---|
| Calculated: | 33.2 | 0.7 | 9.68 | 36.74 |
| Found | 33.5 | 1.1 | 10.1 | 36.9 |

The following description of the preparation of 4,5,6-trichloro-2-trifluoromethyl benzimidazole-1-carboxylic acid methyl ester from 4,5,6-trichloro-2-trifluoro benzimidazole and chloroformic acid methyl ester via the sodium salt of the former will serve to illustrate the process according to the invention.

A quantity of 16 grams (0.05 mole) of 4,5,6-trichloro-2-trifluoromethyl benzimidazole was dissolved in 80 milliliters of absolute acetone and reacted at room temperature with 4.13 grams (0.05 mole) of 90% sodium ethylate with stirring for 2 hours.

The reaction mixture was thereafter mixed at 40° C with 5.56 grams (0.05 mole) of chloroformic acid methyl ester while stirring. The reaction mixture was stirred at 40° C for a further 10 hours and subsequently filtered off from the sodium chloride which had formed, the solvent evaporated and the residue recrystallized rom ligroin (80°–100° C). Yield: 17.3 grams (49.5%) of 2-trifluoromethyl-4,5,6-trichloro-1-benzimidazole carboxylic acid methyl ester having a melting point of 137°–141° C. The thin layer chromatogram showed the compound to a homogeneous substance. As regards mixed melting point and thin layer chromatogram it was identical with a reference sample prepared from authentic 3,4,5-trichloro phenylene diamine by means of trifluoro acetic and subsequent carbomethoxylation.

The substituted benzimidazole-1-carboxylic acid esters listed in the following Table were prepared as novel compounds according to the process described above:

TABLE I

| Compound No. | Identity, referring to formula I | Melting Point ° C |
|---|---|---|
| 1 | R = ethyl<br>R' = –CF$_3$<br>R'' = Cl(5)* | 48–50 |
| 2 | R = ethyl<br>R' = CF$_3$<br>R'' = Cl$_3$ (4,5,6) | 110–113 |
| 3 | R = methyl<br>R' = –CF$_3$<br>R'' = Cl$_3$ (4,5,6) | 137–141 |
| 4 | R = isobutyl<br>R' = –CF$_3$<br>R'' = Cl$_3$ (4,5,6) | 89–91 |
| 5 | R = phenyl<br>R'' = –CF$_3$<br>R'' = Cl$_3$ (4,5,6) | 138–141 |
| 6 | R = allyl<br>R' = –CF$_3$<br>R'' = Cl$_3$ (4,5,6) | 73–75 |
| 7 | R = 2-chloroethyl<br>R' = –CF$_3$<br>R'' = Cl3 (4,5,6) | 144–146 |
| 8 | R = benzyl<br>R' = –CF$_3$<br>R'' = Cl$_3$ (4,5,6) | 98–99 |
| 9 | R = 2-bromoethyl<br>R' = –CF$_3$<br>R'' = Cl$_3$ (4,5,6) | 133.5–135.5 |
| 10 | R = isopentyl<br>R' = –CF$_3$<br>R'' = Cl$_3$ (4,5,6) | 72.5–73.5 |
| 11 | R = 2-methallyl<br>R' = –CF$_3$<br>R'' = Cl$_3$ (4,5,6) | 90–91 |
| 12 | R = propyl<br>R' = –CF$_3$<br>R'' = Cl$_3$ (4,5,6) | 95–96 |
| 13 | R = isopropyl<br>R' = –CF$_3$<br>R'' = Cl$_3$ (4,5,6) | 135.5–136 |
| 14 | R = 2-ethoxyethyl<br>R' = –CF$_3$<br>R'' = Cl$_3$ (4,5,6) | 89.5–90.5 |
| 15 | R = hexyl<br>R' = –CF$_3$<br>R'' = Cl$_3$ (4,5,6) | 66.5–67.5 |
| 16 | R = cyclopentyl<br>R' = –CF$_3$<br>R'' = Cl$_3$ (4,5,6) | 127.5–128.5 |
| 17 | R = 1,2-dimethylpropyl<br>R' = –CF$_3$<br>R'' = Cl$_3$ (4,5,6) | 123–124 |
| 18 | R = cyclohexylmethyl<br>R' = –CF$_3$<br>R'' = Cl$_3$ (4,5,6) | 108.5–109 |
| 19 | R = heptyl<br>R' = –CF$_3$<br>R'' = Cl$_3$ (4,5,6) | 48.5–51 |
| 20 | R = decyl<br>R' = –CF$_3$<br>R'' = Cl$_3$ (4,5,6) | 37–39 |
| 21 | R = ethyl<br>R' = Cl<br>R'' = Cl$_3$ (4,5,6) | –139 |
| 22 | R = cycloheptyl<br>R' = –CF$_3$<br>R'' = Cl$_3$ (4,5,6) | 113–114.5 |
| 23 | R = ethyl<br>R' = Cl<br>R'' = NO$_2$(5) | 97 |
| 24 | R = ethyl<br>R' = Cl<br>R'' = Cl(5) | 78 |
| 25 | R = butyl<br>R' = –CF$_3$<br>R'' = Cl$_3$ (4,5,6)<br>R = pentyl | 79.5–80 |

TABLE I-continued

| Compound No. | Identity, referring to formula I | Melting Point °C |
|---|---|---|
| 26 | R' = —CF$_3$<br>R'' = Cl$_3$ (4,5,6)<br>R = 1-methylpropyl | 53–54 |
| 27 | R' = —CF$_3$<br>R'' = Cl$_3$ (4,5,6)<br>R = 3-chloropropyl | 110.5–111 |
| 28 | R' = —CF$_3$<br>R'' = Cl$_3$ (4,5,6)<br>R = 3-bromopropyl | 109–110 |
| 29 | R' = —CF$_3$<br>R'' =Cl$_3$ (4,5,6)<br>R = propyl | 113.5–114.5 |
| 30 | R' = —CF$_3$<br>R'' = Cl$_2$ (4,5,6)<br>R = propyl | 63–64 |
| 31 | R' = CF$_3$<br>R'' = (NO$_2$)$_2$ (4,5,6) | 113–115 |

*Number in parenthesis indicates position on ring.

Compounds of the invention are effective herbicides. This use for these compounds, and herbicidal formulations of them, are claimed in copending application Ser. No. 448,243, filed Apr. 15, 1965, now abandoned.

Compounds of this invention also are effective insecticides, being particularly effective in control of mites. Since the effective insecticides also herbicidal, use of these compounds as insecticides is in general restricted to control of insects in environments not involving living plants. Also, since many, if not most of these insecticides are only moderately toxic to mammals, they may find application in the control of insects, particularly mites, that infest animals, such as pets, livestock and other domesticated or caged animals. In addition to their high araricidal activity, compounds of the invention show a wide range of activity against caterpillars and phyllophagous pests. Some have high ovicidal activity.

Table II shows the activity of typical esters of the invention with respect to larvae of the diamond back moth (*Plutella maculipennis Curt.*) and with respect to two-spotted spider mites (*Tetranychus telarius L.*). The toxicity is described in terms of a Toxicity Index (T.I.), which indicates as relative value the toxicity index defined by Sun (J. Econ. Entom. 43, 45 (1950)) as the ratio of the LC$_{50}$ dosage (median value of the concentration required to cause 50% mortality of the test insect) of a standard insecticide relative to that of the test compound:

$$T.I. = \frac{LC_{50} \text{ standard insecticide}}{LC_{50} \text{ insecticide under test}} \cdot 100$$

In each case the toxicity index of the standard insecticide is made equal to 100 so that a test compound which is more active than the chosen standard insectide shows an index above 100, whereas the index value of compounds which display a lower activity than the standard insecticide will be below 100.

This way of expressing the activity in relative values not only provides a direct and convenient comparison of the insecticidal activity of the individual organic compounds and makes it possible for the relative activity of an insecticide, compared with a selected standard insecticide, to be applied to a different standard by simple conversion, but in addition largely eliminates the differences which on comparing absolute values may occur during various determinations owing to physical factors (variations in spraying volumes, drop size, spraying pressure, etc.) as well as biological factors (such as determination of the mortality criterion, differences in age, size of species, etc.).

The standard insecticide used against *Plutella maculipennis Curt.* was endrin, and in the test with *Tetranychus telarius* methylparathion was employed.

The tests were carried out as follows: the compounds to be tested were dissolved in 2 milliliters of acetone containing 0.25% or 0.5% of a commercial dispersing agent and made up with water to 10 milliliters total volume.

Tests with diamond back moths

All the leaves but one of 2–3 weeks old turnips (*Brassica rapa*) were removed and the surface of the soil was covered with a sheet of protective cardboard provided with holes for the stems of the plants.

The plants were sprayed with the dispersion containing the active compound by means of a spraying machine operating on the conveyor belt principle, which machine permits of continuous spraying with logarithmically decreasing concentrations. After being sprayed the plants were allowed to develop under normal greenhouse conditions (24° ± 2° C) with varying humidity and after drying of the sprayed film each covered with ten 8-days' old larvae of the diamond back moth (of mixed sex). 24 hours after the larvae had been applied their mortality was determined and the concentration at which 50% of the larvae were killed was used as LC$_{50}$-value for calculating the toxicity index.

Tests with two-spotted spider mites

From the leaves of bean plants (*Phaseolus vulgaris*) discs with a diameter of about 3 cm were cut, placed on filter paper which was kept moist by a wad of cotton wool immersed in water, after which each of the leaf segments was infested with 10 adults 2–3 day-old mites. The leaf discs were sprayed with the emulsion containing the test compound as described in the foregoing test. After being sprayed the leaf discs were kept under the same greenhouse conditions as above, and after 24 hours a mortality count was made of the mites.

In all the series of tests a standard insecticide was used as control.

Column 4 of Table II gives the acute oral toxicity (LC$_{50}$ dosage, milligrams test compound per kilogram of animal body weight) to warm-blooded animals for a number of the esters of the invention. Mice were used as the test animal.

TABLE II

| | Test Insect | | Toxicity to warm-blooded animals |
|---|---|---|---|
| Compound | Plutella maculipennis | Tetranychus telarius | |
| 2 | 200 | 800 | 400 |
| 3 | 250 | 500 | 50 |
| 4 | 250 | 500 | 100–200 |
| 5 | 200 | 200 | 50–100 |
| 6 | 250 | 300 | 50–100 |
| 7 | 150 | 250 | — |
| 8 | 100 | 200 | — |
| 9 | 100 | 50 | 100 |
| 10 | 100 | 350 | — |
| 11 | 100 | 400 | — |
| 12 | 150 | 1400 | 400 |
| 13 | 80 | 1200 | — |
| 14 | 150 | 500 | — |
| 15 | 150 | 600 | 127 |
| 16 | 60 | 300 | 368 |
| 17 | 50 | 500 | 808 |
| 18 | 100 | 7 | 187 |
| 19 | 150 | 150 | — |
| 25 | 150 | 900 | — |

| | Test Insect | | Toxicity |
| Compound | Plutella maculipennis | Tetranychus telarius | to warm-blooded animals |
| --- | --- | --- | --- |
| 26 | 200 | 900 | — |

The ovicidal activity of a representative of the esters of the invention, viz. compound 2, was determined as follows: 10 adult two-spotted mites (*Tetranychus telarius*) were placed in each case on round leaf discs of bean leaves (*Phaseolus vulgaris*) and left there for 24 hours for egg laying. The mites were subsequently removed and the eggs counted. The number of eggs varied 50 and 100 per leaf and averaged about 80. As in the foregoing tests, the leaf discs were sprayed with solutions containing decreasing concentrations of active compounds. After a weak the hatched eggs were counted and the result expressed as the concentration ($LC_{50}$ grams/100 milliliters of solution) which effected a 50% kill of the eggs.

It was found that the $LC_{50}$ dosage of compound 2 was 0.0062 grams/100 milliliters of solution. Thus, compound 2 highly ovicidal with respect to these mites.

In most cases the substituted benzimidazole-1-carboxylic acid esters according to the invention are solid substances, which are readily soluble in acetone, alcohols and ligroin. On account of their low volatility they are remarkable for their long active life.

The active compounds according to the invention may be formulated with gaseous, liquid or solid carriers in generally known formulations. If desired, they may contain other ingredients, for example, emulsifiers, dispersion agents as well as sticking improvers. Examples of suitable forms in which the compounds are used are: dusts, suspensions, emulsions, solutions, aerosols, fumigants or pastes.

We claim as our invention:

1. A method for controlling insects comprising subjecting insects to an insecticidally effective amount of a benzimidazole of the formula

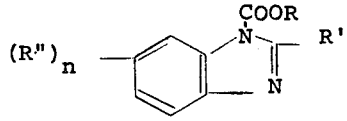

wherein R is alkyl, alkenyl, cycloalkyl, aryl, aralkyl or alkaryl of up to 8 carbon atoms, R' is perhaloalkyl of 1–4 carbon atoms, R'' is chlorine or bromine and n is a whole number of 2 to 4.

2. The method of claim 1, wherein the R substituent of the benzimidazole is an alkyl of 1–4 carbon atoms, R' is trifluoromethyl, R'' is chlorine and n is 3.

3. An insecticidal composition comprising an insecticidally effective amount of a benzimidazole of the formula

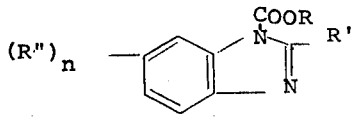

wherein R is alkyl, alkenyl, cycloalkyl, aryl, aralkyl or alkaryl of up to 8 carbon atoms, R' is perhaloalkyl of 1–4 carbon atoms, R'' is chlorine or bromine and n is a whole number of 2 to 4.

4. The composition of claim 3 wherein the R substituent of the benzimidazole is an alkyl of 1–4 carbon atoms, R' is trifluoromethyl, R'' is chlorine and n is 3.

5. A method for the control of acarids which comprises contacting the acarids with an acaricidally effective amount of a compound of the formula:

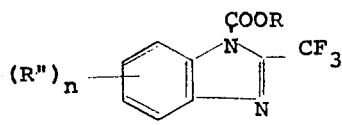

wherein R is a member selected from the group consisting of alkyl of 1 to 12 carbon atoms, halo substituted lower alkyl, phenyl, lower alkylphenyl, naphthyl, and cyclohexyl, and wherein R'' is a member selected from the group consisting of halo, nitro, and cyano, and wherein n is an integer of 1 to 4.

* * * * *